United States Patent [19]

Grandadam et al.

[11] 4,100,297
[45] Jul. 11, 1978

[54] NOVEL ANTI-ACARID METHODS

[75] Inventors: Jean André Grandadam, Saint-Maur des Fosses; Simone Heurtaux, Clichy-sous-Bois, both of France

[73] Assignee: Roussel Uclaf, Paris, France

[21] Appl. No.: 770,303

[22] Filed: Feb. 22, 1977

[30] Foreign Application Priority Data

Feb. 19, 1976 [FR] France .................... 76 04560

[51] Int. Cl.² ............... A61K 31/275; A61K 31/215
[52] U.S. Cl. .................................. 424/304; 424/306
[58] Field of Search ............................ 424/306, 304

[56] References Cited

U.S. PATENT DOCUMENTS

| 3,720,703 | 3/1973 | Elliott et al. | 424/306 |
| 4,012,522 | 3/1977 | Searle et al. | 424/306 |

Primary Examiner—Sam Rosen
Attorney, Agent, or Firm—Hammond & Littell

[57] ABSTRACT

Novel antiacaridal composition comprising an effective amount of at least one compound selected from the group consisting of cis and trans, racemic and optically active isomers of a compound of the formula

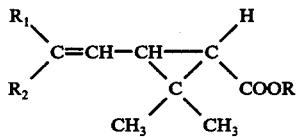

wherein $R_1$ is selected from the group consisting of hydrogen, halogen and alkyl of 1 to 8 carbon atoms, $R_2$ is selected from the group consisting of hydrogen, halogen, alkyl of 1 to 8 carbon atoms and alkoxy carbonyl of 2 to 8 carbon atoms and $R_1$ and $R_2$ taken together with the carbon atom to which they are attached form a cycloalkyl of 3 to 6 carbon atoms and R is selected from the group consisting of

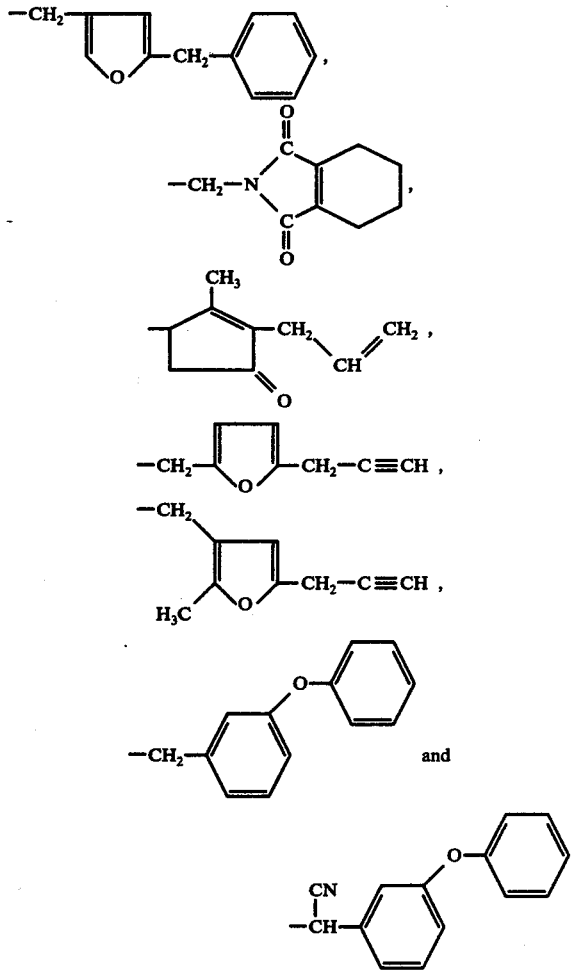

and a pharmaceutical carrier and to a method of combatting acarids in warm-blooded animals.

16 Claims, No Drawings

NOVEL ANTI-ACARID METHODS

OBJECTS OF THE INVENTION

It is an object of the invention to provide novel antiacaridal compositions based on pyrethrinoids.

It is a further object of the invention to provide a novel method of combatting acarids in warm-blooded animals.

These and other objects and advantages of the invention will become obvious from the following detailed description.

THE INVENTION

The novel and antiacaridal compositions of the invention are comprised of an antiacaridally effective amount of at least one compound selected from the group consisting of cis and trans, racemic and optically active isomers of a compound of the formula

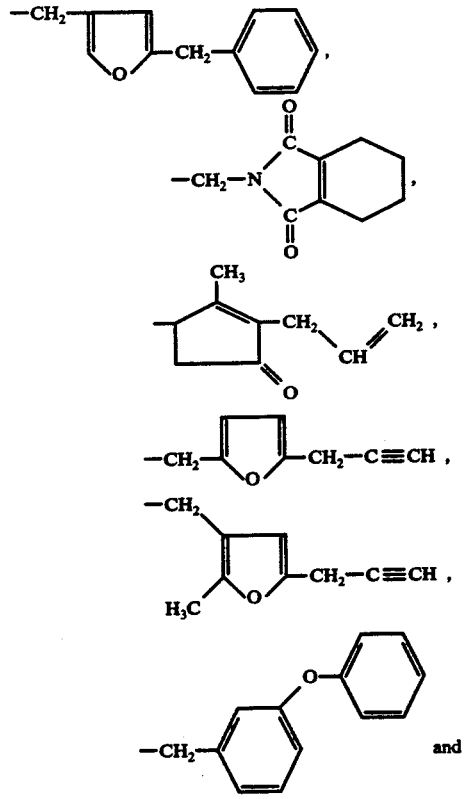

wherein $R_1$ is selected from the group consisting of hydrogen, halogen and alkyl of 1 to 8 carbon atoms, $R_2$ is selected from the group consisting of hydrogen, halogen, alkyl of 1 to 8 carbon atoms and alkoxy carbonyl of 2 to 8 carbon atoms and $R_1$ and $R_2$ taken together with the carbon atom to which they are attached form a cycloalkyl of 3 to 6 carbon atoms and R is selected from the group consisting of

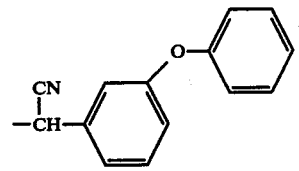

and a pharmaceutical carrier.

When $R_1$ and $R_2$ are halogen, the are preferably chlorine or bromine and when they are alkyl, they are preferably methyl, ethyl, n-propyl or n-butyl. When $R_2$ is alkoxy carbonyl, it is preferably methoxycarbonyl, ethoxycarbonyl, propoxycarbonyl or butoxycarbonyl. When $R_1$ and $R_2$ and the carbon atom to which they are attached form a cycloalkyl, it is preferably cyclopropyl.

Among the preferred compositions of the invention are those where $R_1$ and $R_2$ are alkyl of 1 to 8 carbon atoms, those where $R_1$ and $R_2$ are chlorine, those where $R_1$ and $R_2$ are bromine and those where $R_1$ and $R_2$ together with the carbon atom to which they are attached are cycloalkyl of 3 to 6 carbon atoms.

Among the preferred compositions of the invention are those containing at least one compound of formula I or mixtures thereof except for those compounds where $R_1$ and $R_2$ both represent chlorine or both represent methyl where R is 3-phenoxybenzyl or α-cyano-3-phenoxybenzyl, those compositions wherein $R_1$ and $R_2$ are alkyl of 1 to 8 carbon atoms but $R_1$ and $R_2$ are not both methyl where R is 3-phenoxybenzyl or α-cyano-3-phenoxybenzyl and those compositions wherein $R_1$ and $R_2$ are chlorine and R is other than 3-phenoxybenzyl or α-cyano-3-phenoxybenzyl.

Among the preferred compositions of the invention are those containing compounds of formula I wherein R is

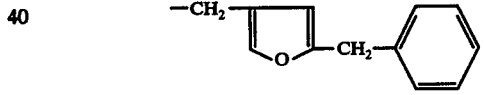

in cis or trans form, racemic mixtures or optically active isomers or mixtures thereof, or is

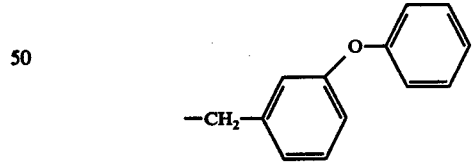

in cis or trans form, racemic mixtures or optically active isomers or mixtures thereof or is

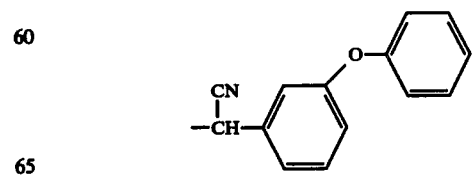

in cis or trans form, racemic mixtures or optically active isomers or mixtures thereof. Especially preferred are the compounds of formula I wherein R is 3-phenoxybenzyl or α-cyano-3-phenoxybenzyl with the proviso that $R_1$ and $R_2$ are not both chlorine or both methyl.

Another preferred group of compositions are those wherein R is

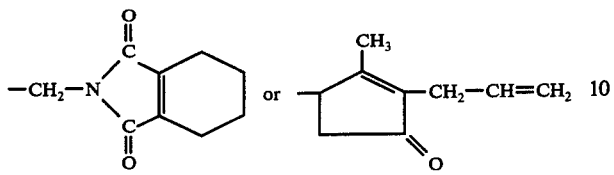

with a cis or trans form, racemic mixture or optically active isomer or mixtures thereof.

The most preferred compositions contain as the active ingredient a compound selected from the group consisting of 3-phenoxybenzyl 2,2-dimethyl-3S-(2',2'-dichlorovinyl)-cyclopropane-1R-carboxylate, (±) α-cyano-3-phenoxybenzyl 2,2-dimethyl-3R-(2',2'-dibromovinyl)-cyclopropane-1R-carboxylate, (±) α-cyano-3-phenoxybenzyl 2,2-dimethyl-3R-(2',2'-dichlorovinyl)-cyclopropane-1R-carboxylate, 5-benzyl-3-furylmethyl 2,2-dimethyl-3R-cyclopentylidenemethyl-cyclopropane-1R-carboxylate or mixtures of the said compounds, as well as racemic or optically active isomer, cis or trans 5-benzyl-3-furylmethyl chrysanthemates or mixtures thereof or 5-benzyl-3-furylmethyl d-trans-chrysanthemate.

Among the mixtures of d-trans and d-cis or dl-trans and dl-cis 5-benzyl-3-furylmethyl chrysanthemate are mentioned particularly those containing 5 to 95% of d-trans or dl-trans 5-benzyl-3-furylmethyl chrysanthemate and 95 to 5% of d-cis or dl-cis 5-benzyl-3-furylmethyl chrysanthemate.

Also a preferred embodiment of the invention are the compositions containing as the active ingredient (−) α-cyano-3-phenoxybenzyl 2,2-dimethyl-3R-(2',2'-dibromovinyl)-cyclopropane-1R-carboxylate or (S)-allethrolone d-transchrysanthemate or neopynaminol d-trans-chrysanthemate.

The compounds of formula I are known compounds and may be prepared by the process of French Patent No. 1,503,260. They are known for their insecticidal activity and are frequently used to combat insects such as flies, beetles and cockchafers.

It has now been discovered that the composition of the invention possess antiacaridal activity and can be used more especially in veterinary medicine to combat particularly all sorts of mange such as sarcoptic mange, psoroptic mange and chorioptic mange while ensuring a rapid disappearance of pruritus and healing of lesions. The compositions are also useful against ticks, such as Boophilus species, Hyalomma species, Amblyomma species and Rhipicephalus species. The compositions have an excellent cutaneous and general tolerance. It is particularly possible to treat a great number of animals in the same stable without any inconvenience.

The preferred compositions of the invention possess besides the compound of formula I a synergist such as α-[2-(2-butoxyethoxy)-ethoxy]-4,5-methylene dioxy-2-propyltoluene or piperonyl butoxide, or the 2,3-dicarboximide of N-(2-ethylbenzyl)-bicyclo (2,2,1)-hepta-5-ene-anhydrophthalic acid preferably in a weight ratio of synergist to compound of formula I of 2 to 15:1, most preferably 3 to 7:1.

The compositions may be prepared in the usual form of veterinary products. For local application, for example, the compositions may be in the form of solutions emulsifible with water for dilution at the time of use. Generally, they contain 1/500 to 1/5 by weight of the active principle, preferably 1/100 to 1/10. The solutions can also contain a quantity of synergist agent for pyrethrinoids as indicated above such as one part by weight of the compound of formula I per 2 to 15 parts, preferably 3 to 7 parts by weight of piperonyl butoxide.

The compositions usually also contain an emulsifier such as Tween or Span. Preferably, nonionic emulsifiers such as Polysorbate 80 or Triton X-100 are used and the emulsifiers act in the role of aiding wetting and penetration of the active compound in the lesions of the skin. The amount of emulsifier is preferably 1 part by weight of active compound per 2 to 20, preferably 5 to 10, parts by weight of emulsifier. The compositions may also contain an antioxidant agent soluble in organic solvents such as Tocopherol acetate.

The active ingredient and the other ingredients such as synergists, emulsifiers and antioxidants are generally in solution in an alcohol such as ethanol or a mixture of ethanol and isopropanol or a mixture of ethanol, isopropanol and ethyl acetate.

The dosage for external use will vary with the animal being treated and the parasites carried thereby. For example, 5-benzyl-3-furylmethyl d-trans chrysanthemate is advantageously used in solution at a concentration of 1/1000 and (−) α-cyano-3-phenoxybenzyl 2,2-dimethyl-3R-(2',2'-dichlorovinyl)-cyclopropane-1R-carboxylate is preferably used at a concentration of 1/10,000.

For subcutaneous or intramuscular use, the compounds of formula I may be used in solution with a conventional excipient such as a mixture of benzyl benzoate and arachide oil. Injectable solutions can equally contain α-tocopherol acetate and piperonyl butoxide. For oral use, the compositions may be in the form of capsules.

It is convenient for veterinary use to use the compounds of formula I in admixture with balanced feeds for the animal which feed components for the animals are constituted of a balanced feed for animals which contain one or more of the compounds of formula I. Examples of suitable feeds are those containing 0.004 to 0.2% by weight of (−) α-cyano-3-phenoxybenzyl 2,2-dimethyl-3R-(2',2'-dibromovinyl)-cyclopropane-1R-carboxylate or 0.04 to 10% by weight of 5-benzyl-3-furylmethyl d-trans-chrysanthemate or 0.04 to 0.3% by weight of (S) allethrolone d-trans chrysanthemate or 0.03 to 7.5% by weight of neopynaminol d-trans-chrysanthemate. The animal feeds may also contain a synergist. The novel method of combatting acaridal infections in warm-blooded animals comprises administering to warm-blooded animals an antiacaridally effective amount of at least one compound of formula I, preferably with a synergist, most preferably with piperonyl butoxide. The compounds may be administered particularly to farm animals such as bovines, sheep, pigs and poultry parenterally, orally, rectally or topically. The dosage will vary depending on the parasite and the product.

For example, to attack mange in bovines by oral administration, the dosage may be 0.20 to 0.80 g/kg of body weight of 5-benzyl-3-furylmethyl d-trans chrysanthemate, 0.003 to 0.013 g/kg of body weight of (−) α-cyano-3-phenoxybenzyl 2,2-dimethyl-3R-(2',2'-dibromovinyl)-cyclopropane-1R-carboxylate, 0.02 to 0.08 g/kg of body weight of (S)-allethrolone d-trans chrysanthemate or 0.4 to 3 g/kg of body weight of neopynaminol d-trans chrysanthemate.

Chronic toxicity studies on rats show that at these doses there is no danger to the animals. Orally administered doses to rats of 2 g/kg of body weight of 5-benzyl-3-furylmethyl d-trans-chrysanthemate, of 0.010 g/kg of body weight of (−) α-cyano-3-phenoxybenzyl 2,2-dimethyl -3R-(2',2'-dibromovinyl)-cyclopropane-1R-carboxylate, of 0.075 g/kg of body weight of (S) allethrolone d-trans chrysanthemate and of 2 g/kg of body weight of neopynaminol d-trans chrysanthemate were well tolerated in chronic toxicity tests.

The method of the invention is particularly directed to treating farm animals for psoroptic mange with (−) α-cyano-3-phenoxybenzyl 2,2-dimethyl-3R-(2',2'-dibromovinyl)-cyclopropane-1R-carboxylate or 5-benzyl-3-furylmethyl d-trans chrysanthemate or (S) allethrolone d-trans chrysanthemate or neopynaminol d-trans chrysanthemate or mixtures thereof. The said compounds may be administered topically, parenterally, or orally.

In the following examples there are described several preferred embodiments to illustrate the invention. However, it should be understood that the invention is not intended to be limited to the specific embodiments.

EXAMPLE 1

A solution was prepared with 5 g of 5-benzyl-3-furylmethyl d-trans chrysanthemate, 25 g of piperonyl butoxide, 10 g of Polysorbate 80 [polyoxyethylene (20) sorbitan monooleate], 25 g of Triton X-100 [condensation of ethylene oxide-octylphenol], 1 g of tocopherol acetate and sufficient ethanol for 100 ml and the concentrate was diluted with 5 liters of water just before use.

EXAMPLE 2

A solution was prepared with 0.5 g of (−)α-cyano -3-phenoxybenzyl 2,2-dimethyl-3R-(2',2'-dibromovinyl)cyclopropane-1R-carboxylate, 2.5 g of piperonyl butoxide, 10 g of Polysorbate 80, 25 g of Triton X-100, 1 g of tocopherol acetate and sufficient ethanol for 100 ml and the concentrate was diluted with 5 liters of water just before use.

EXAMPLE 3

A solution was prepared with 2 g of 3-phenoxybenzyl 2,2-dimethyl-3R-(2',2'-dibromovinyl)-cyclopropane-1R-carboxylate, 10 g of piperonyl butoxide, 10 g of Polysorbate 80, 25 g of Triton X 100, 0.4 g of tocopherol acetate, 0.4 g of citric acid and sufficient ethanol to obtain 100 ml and the concentrate was diluted with water before use.

EXAMPLE 4

A solution was prepared with 5 g of neopynaminol d-trans chrysanthemate, 25 g of piperonyl butoxide, 15 g of Polysorbate 80, 20 g of Triton X-100, 1 g of tocopherol acetate and sufficient ethanol to obtain 100 ml and the concentrate was diluted before use with water.

EXAMPLE 5

A solution was prepared with 5 g of (S) allethrolone d-trans chrysanthemate, 25 g of piperonyl butoxide, 10 g of Polysorbate 80, 25 g of Triton X-100, 1 g of tocopherol acetate and sufficient ethanol for 100 ml.

EXAMPLE 6

An injectable solution was prepared with 2 g of 5-benzyl-3-furylmethyl d-trans chrysanthemate, 6.65 g of piperonyl butoxide, 6.33 g of α-tocopherol acetate, 29 g of benzyl benzoate and sufficient arachide oil to obtain 100 ml.

EXAMPLE 7

An injectable solution was prepared with 0.03 g of (−) α-cyano-3-phenoxybenzyl 2,2-dimethyl-3R-(2',2'-dibromovinyl)-cyclopropane-1R-carboxylate, 1 g of piperonyl butoxide, 0.15 g of α-tocopherol acetate, 29 g of benzyl benzoate and sufficient arachide oil for 100 ml.

EXAMPLE 8

An injectable solution was prepared with 0.2 g of (S) allethrolone d-trans chrysanthemate, 0.6 g of piperonyl butoxide, 0.25 g of α-tocopherol acetate, 29 g of benzyl benzoate and sufficient arachide oil for 100 ml.

EXAMPLE 9

An injectable solution was prepared with 4 g of neopynaminol d-trans chrysanthemate, 12 g of piperonyl butoxide, 1 g of α-tocopherol, 29 g of benzyl benzoate and sufficient arachide oil for 100 ml.

EXAMPLE 10

Capsules were prepared containing 1 g of (−) α-cyano-3-phenoxybenzyl 2,2-dimethyl-3R-(2',2'-dibromovinyl)-cyclopropane-1R-carboxylate and excipient.

EXAMPLE 11

A balanced feed base comprising corn, dehydrated alfalfa, wheat stalks, palmiste molasses cake, urea and a mineral vitamin condiment contained a minimum of 11% raw protein material (2.8% apportional to urea) and 2.5% of fatty material and a maximum of 15% of celullosic material, 6% of mineral material and 13% of moisture. The said feed base corresponded to 82 forage units per 100 kilos and contained 910,000 I.U. of vitamin A, 91,000 I.U. of vitamin $D_3$, 156 mg of vitamin E and 150 mg of vitamin C per 100 kilos, 0.3 kg of 5-benzyl-3-furylmethyl d-trans chrysanthemate was incorporated to make 100 kg of the feed in all.

EXAMPLE 12

Using the feed base of Example 11, there was incorporated to make 100 kg of the feed in all either 0.04 kg of (−) α-cyano-3-phenoxybenzyl 2,2-dimethyl-3R-(2',2'-dibromovinyl)-cyclopropane-1R-carboxylate or 0.2 kg of (S) allethrolone d-trans chrysanthemate or 0.25 kg of neopynaminol d-trans chrysanthemate.

EXAMPLE 13

Clinical study of cattle attacked by psoroptic mange 50 bull-calves weighing between 550 to 600 kg were attacked by psoroptic mange and samples were taken by scraping until rose blood at several points to gauge the lesions before the treatment and then 5, 15 and 25 days after the first treatment. A solution of Example 1 was diluted with 5 liters of water to obtain a concentration of 5-benzyl-3-furylmethyl d-trans chrysanthemate of 1 part per 1000 and the solution was applied to the lesions three times at 10 days intervals on days Day 0, Day 10 and Day 20. Before treatment, 25 samples were positive as noted by the presence of living psoroptes and on the 5th day after the first treatment, the pruritis of all the animals disappeared, the skin began to assume a normal aspect and only 3 cows out of the 50 showed the parasites in the lesions. 15 and 25 days after the start of treatment, there were no living psoroptes and the cutaneous tolerance was very good. The conclusion is that 5-benzyl-3-furylmethyl d-trans chrysanthemate when applied locally in solution at a concentration of 1/1000 was effective against mange.

EXAMPLE 14

Microcapsules containing 20 ml of a solution of 5-benzyl-3-furylmethyl d-trans chrysanthemate diluted as in Example 1 were injected subcutaneously to calves at the base of the ear and the animals were observed for 15 days during which there was no reddening, no pruritis, no depilation and no fever. This means that the composition was perfectly tolerated.

EXAMPLE 15

6 young bovines of charolaise race were attacked by psoroptic mange and were treated regularly for 4 months with commercially available ixodicides. In spite of the treatments, the bovines were very heavily infected with parasites at the end of the 4 months. It was ascertained that the animals were attacked generally by mange with zones of scaly dermitis and thickening of the skin (rhinoceros skin) and a serious inflammation of the skin and epidermic placard peeling off was observed. In certain places, the skin was literally destroyed, excorticated, oozing and bleeding. All animals were subjected to a very important thinness and samples taken from the depth of the mange lesions showed the presence of a very large number of acarids of the Posropte genus.

Each of the bovines were sprayed with 1½ liters of aqueous solution of (−) α-cyano-3-phenoxybenzyl 2,2-dimethyl-3R-(2′,2′-dibromovinyl)-cyclopropane-1R-carboxylate at a concentration of 1/10,000. After 12 days, it was ascertained that there was a clear improvement of the level of the skin and disappearance of pruritis. The samples from the lesions showed that there existed in two thirds of the animals living Psoroptes. A second treatment was effected on the 14th day after the first treatment and after another 12 days or on the 26th day after the first treatment, the skin showed normal redevelopment, the hair covered over the old lesions and pruritis had definitely disappeared. The animals were clinically cured and samples did not show any evidence of acariens.

EXAMPLE 16

3 cows of Maine-Anjou race were attacked by mange on the tail, thigh and loins and the bovines showed a scally dermitis, certain portions of the skin excorticated, oozing and bleeding and also noted was the presence of abundant crusts. Parasitic examination before treatment of the 3 bovines showed the presence of acariens of Psoroptes genus. Treatment on Day 0 with a preparation containing 1 ppm of (S) allethrolone d-trans chrysanthemate was effected by energetically brushing onto the mange lesions of the said preparation and local tolerance of the solution was excellent. After 48 hours of the treatment, there was noted a clear clinical amelioration of the mange lesions and pruritis disappeared. Parasitic examination on day 7 showed only one bovine (more attacked) had living Psoroptes.

Cutaneous samples of the bovines were examined with a binocular magnifying glass, the following results were obtained

| Animal | Before Treatment | 8th Day |
| --- | --- | --- |
| 1 | +++ | + |
| 2 | + | − |
| 3 | + | − |

The results of the Table show that the tested compound has good acaracidal activity against Sarcopte mange in bovines.

EXAMPLE 17

The semichronic toxicity of (S) allethrolone d-trans chrysanthemate was determined on rats for a duration of 3 weeks and at a dose of 75 mg/kg of body weight, the product was perfectly well tolerated.

EXAMPLE 18

A bull, a heifer and a cow of the Maine-Anjou race were generally attacked by mange with zones of scaly dermitis and thickening skin and a grave inflammation of the skin and epidermic placard peeling off with the horns and rear members is observed. An examination of epidermic debris showed mange lesions before treatment of the 3 bovines with a presence of living acariens of Psoroptes genus. The treatment was applied on day 0 with a vigorous brushing using 1 liter of a solution containing 1 ppm of neopynaminol d-trans chrysanthemate for each bovine with an overflow largely around the lesions. The tolerance to the preparation was excellent and after 48 hours, the bovines showed the beginning of clinical healing with disappearance of pruritis and a clear amelioration of the mange lesions. Parasitic examination on day 7 showed no evidence of living psoroptes. Examination of Cutaneous samples of the bovines with a binocular magnifying glass showed the following results.

| No. of Animal | Before Treatment | 7th Day |
| --- | --- | --- |
| 1 | +. | − |
| 2 | ++ | − |
| 3 | +++ | − |

The data of the Table shows that the tested compound possessed good acaricidal activity against Sarcoptes of mange in bovines.

Various modifications of the compositions and method of the invention may be made without departing from the spirit or scope thereof and it is to be understood that the invention is intended to be limited only as defined in the appended claims.

We claim:

1. A method of combatting acarids in warm-blooded animals comprising topically applying to warm-blooded animals an antiacaridally effective amount of at least one compound selected from the group consisting of cis and trans, racemic and optically active isomers of a compound of the formula

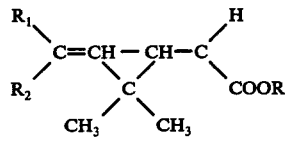

wherein $R_1$ is selected from the group consisting of hydrogen, halogen and alkyl of 1 to 8 carbon atoms, $R_2$ is selected from the group consisting of hydrogen, halogen, alkyl of 1 to 8 carbon atoms and alkoxy carbonyl of 2 to 8 carbon atoms and $R_1$ and $R_2$ taken together with the carbon atom to which they are attached form a cycloalkyl of 3 to 6 carbon atoms and R is selected from the group consisting of

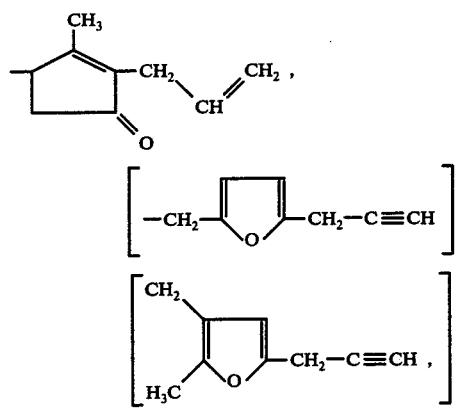

and

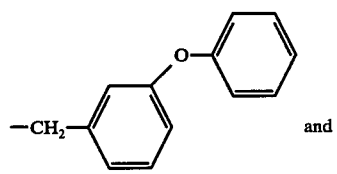

2. A method of claim 1 wherein $R_1$ and $R_2$ are alkyl of 1 to 8 carbon atoms.

3. A method of claim 1 wherein $R_1$ and $R_2$ are chlorine.

4. A method of claim 1 wherein $R_1$ and $R_2$ are bromine.

5. A method of claim 1 wherein $R_1$ and $R_2$ together with the carbon atom to which they are attached form a cycloalkyl of 3 to 6 carbon atoms.

6. A method of claim 1 wherein $R_1$ and $R_2$ are other than both chlorine or both methyl when R is 3-phenoxybenzyl or α-cyano-3-phenoxybenzyl.

7. A method of claim 2 wherein $R_1$ and $R_2$ are other than both methyl when R is 3-phenoxybenzyl or α-cyano-3-phenoxybenzyl.

8. A method of claim 3 wherein R is other than 3-phenoxybenzyl or α-cyano-3-phenoxybenzyl.

9. A method of claim 1 wherein R is

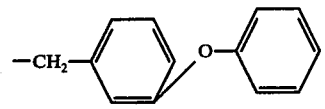

in the cis or trans form, racemic mixtures or optically active isomers and mixtures thereof.

10. A method of claim 1 wherein R is

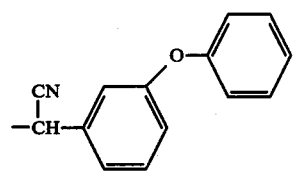

in the cis or trans form, racemic mixtures or optically active isomers and mixtures thereof.

11. A method of claim 9 wherein $R_1$ and $R_2$ are other than both methyl or both chlorine.

12. A method of claim 10 wherein $R_1$ and $R_2$ are other than both chlorine or both methyl.

13. A method of claim 1 wherein R is

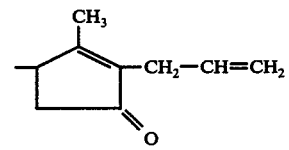

in the cis or trans form, racemic mixtures or optically active isomers and mixtures thereof.

14. A method of claim 1 wherein the active compound is at least one compound selected from the group consisting of 3-phenoxybenzyl 2,2-dimethyl-3S-(2',2'-dichlorovinyl)-cyclo-propane-1R-carboxylate, (±) α-cyano-3-phenoxybenzyl 2,2-benzyl 2,2-dimethyl-3R-(2',2'-dibromovinyl)-cyclopropane-1R-carboxylate, (±) α-cyano-3-phenoxybenzyl 2,2-dimethyl-3R-(2',2'-dichlorovinyl)-cyclopropane-1R-carboxylate and 3-phenoxybenzyl 2,2-dimethyl-3R-(2',2'-dichlorovinyl)-cyclopropane-1R-carboxylate.

15. A method of claim 1 wherein the active ingredient is selected from the group consisting of (—) α-cyano-3-phenoxybenzyl 2,2-dimethyl-3R-(2',2'-dibromovinyl)-cyclopropane-1R-carboxylate, (S)-allethrolone d-trans chrysanthemate and neopynaminol d-trans chrysanthemate.

16. A method of claim 1 comprising the use of a synergist agent.

* * * * *

UNITED STATES PATENT OFFICE
CERTIFICATE OF CORRECTION

Patent No. 4,100,297           Dated July 11, 1978

Inventor(s) Jean-Andre Grandadam, Simone Heurtaux

It is certified that error appears in the above-identified patent and that said Letters Patent are hereby corrected as shown below:

| Col. | Line | Page | Line | |
|------|------|------|------|---|
| 3 | 24 | 5 | 10 | After "carboxylate" insert --3-phenoxybenzyl 2,2-dimethyl-3R-(2',2'-dichlorovinyl)-cyclopropane-1R-carboxylate-- |

Col. 9, lines 25-34, delete the bracketed formulas.

Signed and Sealed this

Twentieth Day of February 1979

[SEAL]

Attest:

RUTH C. MASON
*Attesting Officer*

DONALD W. BANNER
*Commissioner of Patents and Trademarks*